United States Patent [19]

Mumford

[11] Patent Number: 5,100,428
[45] Date of Patent: Mar. 31, 1992

[54] DISPOSABLE TWO PART BODY PRICKER

[75] Inventor: Ernest J. Mumford, Witney, United Kingdom

[73] Assignee: Owen Mumford Limited, Woodstock, United Kingdom

[21] Appl. No.: 628,925

[22] Filed: Dec. 11, 1990

[30] Foreign Application Priority Data

Dec. 12, 1989 [GB] United Kingdom ............... 8928076

[51] Int. Cl.5 .............................. A61B 17/32
[52] U.S. Cl. .................................... 606/182
[58] Field of Search .................. 606/181-183

[56] References Cited

U.S. PATENT DOCUMENTS

| | | | |
|---|---|---|---|
| 3,659,608 | 5/1972 | Perry | 606/182 |
| 4,414,975 | 11/1983 | Ryder et al. | 606/182 |
| 4,452,243 | 6/1984 | Leopoldi et al. | 606/182 |
| 4,539,988 | 9/1985 | Shirley et al. | 606/182 |
| 4,577,630 | 3/1986 | Nitzsche et al. | 606/182 |
| 4,715,374 | 12/1987 | Maggio | 606/182 |
| 4,983,178 | 1/1991 | Schnell | 606/181 |

FOREIGN PATENT DOCUMENTS 0115388 8/1984 European Pat. Off. .
0293092 11/1988 European Pat. Off. .

Primary Examiner—Max Hindenburg
Attorney, Agent, or Firm—Young & Thompson

[57] ABSTRACT

A disposable pricker has a two part body with the parts connected by a hinge (6). A spring (10) and a lancet (1) are entered in one tubular part (7) which is then hinged to a ready position in which the leading end of the lancet, projecting from the tube (7), is confined by guide (17,22) on the other part. The tip (4) of the lancet is protected by a cap (5) which is removed before or as the two parts (7,11) are hinged closely together. This takes the leading end of the lancet clear of the guide (17) and into a passage (13) with a restricted mouth (14). The spring (10), which may be energized at the ready position or by the guide (22) wedging the lancet (1) back, can then act to shoot the lancet (1) forward to cause momentary projection of the tip (4) through the mouth (14). Retraction is assured by the spring (10) or resilient tabs (21) at the mouth.

12 Claims, 2 Drawing Sheets

DISPOSABLE TWO PART BODY PRICKER

FIELD OF THE INVENTION

This invention relates to blood sampling devices, and in particular to a pricker to draw a small drop of blood for analysis. Such prickers are widely used by diabetics, for example, who need to know their sugar level. However, there are many other applications.

BACKGROUND OF THE INVENTION

These days, with AIDS, there is widespread concern surrounding the use of needles and their part in transmitting disease. Once a needle has been used on an infected person, subsequent use or an accidental prick on another could be fatal.

There is therefore a growing demand for a pricker which can be used just once and, having been used, be rendered safe for carriage and disposal. It is the aim of this invention to provide such an instrument.

It would also be advantageous to use known and established products as far as possible, and in particular a lancet of a type we provide for a pricker which is sold under the Registered Trade Mark AUTOLET. Our co-pending European Application No. 90311282.9 describes one possible arrangement, and an alternative is proposed in this specification.

SUMMARY OF THE INVENTION

According to the present invention there is provided a disposable pricker comprising a two-part body and a spring-loaded lancet carried by one part and co-operating with guide means on said other part, said guide means keeping the lancet captive to said one part when the latter is in an initial position, and said one part being movable from that position into a second position in full conjunction with said other part, causing the lancet to be released from the guide means and its tip momentarily to project from said body under the influence of the spring loading.

The guide means may retain the lancet in a primed, spring energised condition when said one part is in said initial position. Alternatively, the guide means may be shaped to cause the lancet to shift relative to said one part, thereby to energise the spring loading, as said one part is moved into said second position.

Preferably, the two parts will be integrally moulded in plastics material, with a thin flexible bridge between them acting as a hinge. The guide means will also conveniently be an integral part of this moulding.

The pricker may be designed to accept a known and established lancet which comprises a generally cylindrical body of moulded plastics material co-axially encasing a needle, the tip of the needle projecting from one end of the body, and initially being protected by an integrally moulded cap breakable from the main body.

For safety, this breaking away of the cap should not be done before the lancet is mounted in the body, and conveniently the first part may have means by which the lancet body can be held by one hand while the cap is removed by the other. Alternatively, the guide means may be arranged to co-operate with the lancet body and cap to remove the cap as said one part is moved to said second position.

The guide means can be shaped to shield the tip so that it is virtually inaccessible when the cap has been removed.

It will be arranged that the lancet tip will retract immediately after its momentary projection so that the tip does not remain exposed and indeed will not accidentally reappear. This may be achieved by the spring which causes the momentary projection being anchored both to the lancet and to said one part. Alternatively, a mouth of said other part through which the tip of the lancet momentarily projects may be provided with a resilient tab which flexes to allow such projection but which immediately bends back to cause the retraction.

Desirably, the two parts will be almost impossible to shift apart after one actuation. They may be locked together in their full conjunction condition by the lancet itself which, having shot forward and retracted a bit, bridges those parts within a virtually closed passage.

BRIEF DESCRIPTION OF THE DRAWINGS

For a better understanding of the invention, one embodiment will now be described, by way of example, with reference to the accompanying drawings, in which.

DETAILED DESCRIPTION OF THE SHOWN EMBODIMENTS

Figure 1:
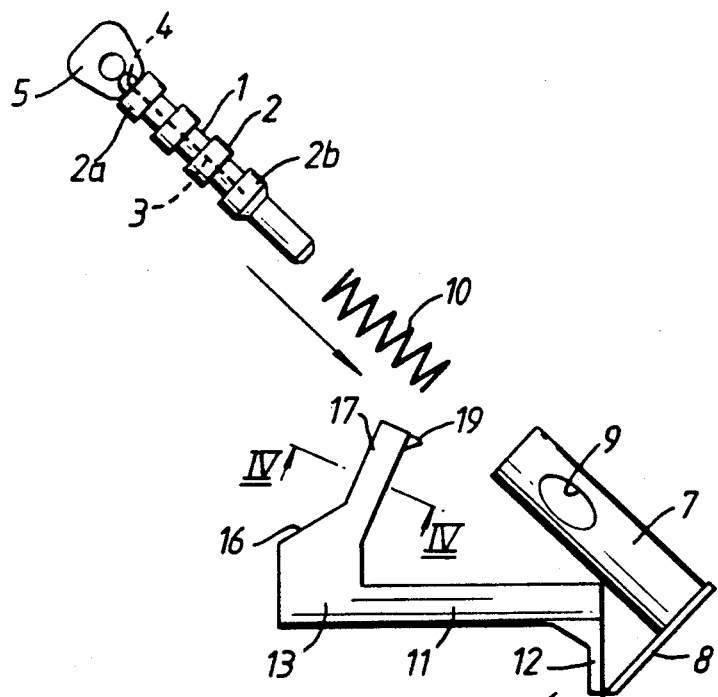
FIG. 1 is a side view of a disposable pricker before assembly.
Figure 2:
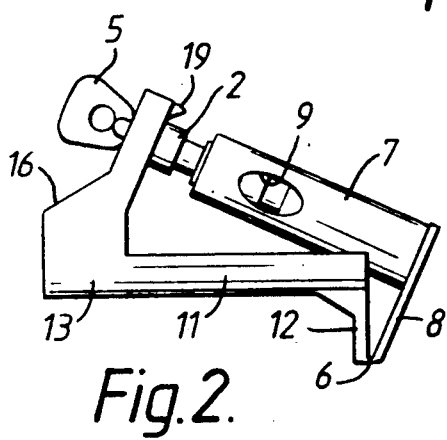
FIG. 2 is a side view of the pricker of FIG. 1 when assembled and ready for use.
Figure 3:
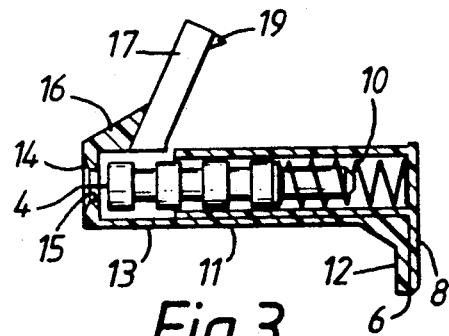
FIG. 3 is an axial section of the pricker at the point of use.

The prickers are intended to use a lancet of known construction which has a moulded plastics body 1 resembling the spool of a spool valve, with several annular ribs 2, the leading one being 2a and the rearmost one 2b. It co-axially encases a needle 3 whose tip 4 is initially shielded by a cap 5 moulded with the body 1 but capable of being broken away.

In FIGS. 2 to 5 the pricker body is in two parts integrally moulded but with a thin web 6 between the parts which enables them to be mutually hinged. The first part is a tube 7 in which the lancet 1 is a loose sliding fit, closed at its rear end by a plate 8 which extends laterally beyond it to the hinge web 6. There is a window 9 in the tube 7 whose purpose is described below. At the production and assembly stage, before the lancet is inserted, a spring 10 is dropped into the tube 7, and it will act between the plate 8 and the rearmost rib 2b in a manner to be described.

The second part of the body has a channel portion 11 of semicircular section, open at the rear end but with a flange 12 that connects it to the hinge web 6. The size of the channel and the position of the hinge is such that the tube 7 can nest within the channel portion 11.

Figure 4:
FIG. 4 is a cross-section, to an enlarged scale, on the line IV—IV of FIG. 1.

At the forward end, the channel portion 11 develops into a short cylinder 13 whose leading end is restricted by an inturned rim 14 presenting a small countersunk hole 15. On the side opposite from the hinge the cylinder 13 is developed into a guide, this comprising a thickened root portion 16 on which there are two projecting parallel fingers 17 angled slightly rearwardly and separated by a narrow slot 18. This slot continues as a groove through the rear of the portion 16 to open into the cylinder 13. The fingers 17 are reduced along their forward inner edges to present a groove or recess leading into the slot 18, as shown in FIG. 4, partially to receive the cap 5 and to shield the tip 4 when the cap is removed. At the tips of the fingers 17 there are small lugs 19 pointing rearwardly.

Figure 5:
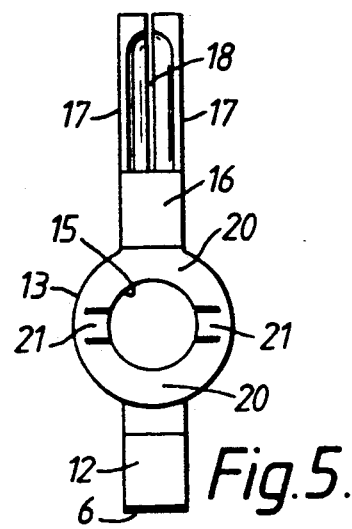
FIG. 5 is an enlarged front end view of the pricker.

The inturned rim 14 may be formed as shown in FIG. 5 to provide means for returning the lancet a short distance immediately after it has made a prick. Instead of being an unbroken annulus, the rim 14 is separated into relative thick rigid portions 20 and thinner resiliently flexible tabs 21 which incline slightly back into the cylinder 13. Two tabs are shown, but one could be sufficient, and there might be more.

Having inserted the spring 10 and the lancet 1 into the tube 7, as indicated by the arrow in FIG. 1, the lancet is pressed rearwardly by its cap 5 while the tube 7 is hinged down towards the channel portion 11. Once the leading rib 2a has gone past the lugs 19, the cap 5 can be released, and so the pricker will then assume and be retained in the FIG. 2 position under spring pressure. It is in this condition that it will be packaged and distributed.

Immediately before use the device is unwrapped and the cap 5 is removed, and this may be done simply by twisting it off. The lancet has to be held to prevent rotation, but finger pressure on it through the window 9 will be sufficient. Then the finger or other part to be pricked is pressed against the hole 15, and the skin bulges in by virtue of the countersinking. Then the tube 7 is snapped towards the channel 11, the tip 4 travelling down the slot 18, and as it enters the cylinder 13, the leading rib 2a is freed from restraint by the guide 16, 17. The spring 10 then shoots the lancet 1 forward, causing the tip 4 momentarily to project. A drop or two of blood is drawn and the operation is complete.

The lancet is caused to be withdrawn immediately by the tabs 21. They flex and allow the leading rib 2 to hit the portions 20 on the forward stroke, but then they assert themselves and push the lancet back just sufficiently for the tip 4 to be withdrawn from the hole 15.

Alternatively, this retraction could be achieved by attaching the rear end of the spring to the base plate 8 and its forward end to the lancet, adjacent the rearmost rib 2b.

It will be seen that, after operation, the lancet locks the two parts of the body together. Its forward end is confined within the cylinder 13, while its rear end remains trapped within the tube 7.

While the hinge 6 has been shown at the rear in this example, there can be many other arrangements. For example, the two main parts may always be parallel and hinged together by a thin web extending lengthwise of them. The guide means would then be curved and centred on the hinge.

It could be arranged by suitable shaping of the guide fingers 17 and the root portion 16 that it would not be necessary to remove the cap 5 in a separate operation. As the tube 7 is forced towards the channel member 11, the cap 5 could be wedged off the main body of the lancet, and it would fly away before the two parts come close to alignment.

In the example described above, the spring has to be compressed as the initial loading and location in the guide is carried out. If accidentally released during this operation, the lancet 1 would be shot clear of the tube 7, and could be lost.

Figure 6:
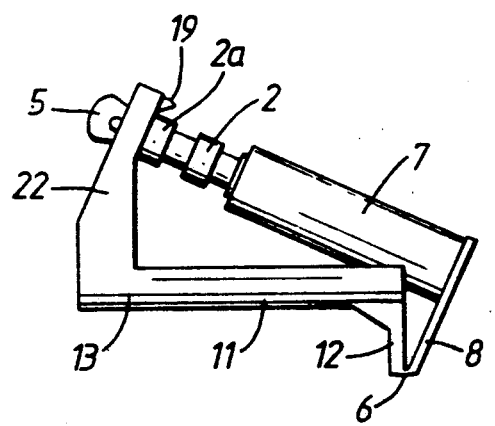
FIG. 6 is a side view of an alternative pricker.

FIG. 6 shows a modified pricker which should avoid this problem, and which will probably be easier to load and operate. Most of the parts are the same and are correspondingly referenced, and the only significant difference lies in the guide, the fingers 22 now being at right angles to the portion 11. This angle is not critical, and the fingers do not have to be straight, but their disposition is such that, at the initial loading position, the spring 10 is only under very light compression and the lancet projects quite substantially from the tube 7. Also, as the tube 7 is pressed into the channel portion 11, so the guide fingers 22, acting on the leading rib 2a, wedge the lancet 1 back into the tube 7, compressing the spring 10. It achieves full compression as the closure motion is completed, and so the lancet is shot forward with the same effect as before.

A minor difference lies in the absence of the window 9; the lancet projects enough to be held between the tube 7 and the guide fingers 22.

I claim:

1. A disposable pricker comprising a two part body and a lancet, the parts being movable with respect to one another from an initial to a second position, one part being adapted to carry the lancet with a tip at its forward end and having spring means to urge the lancet in its forwards direction, and the other part having guide means which co-operate with the forward end of the lancet to retain the lancet retracted in said one part at the initial position and as the parts are moved towards the second position, but to relinquish such retention as the second position is reached, whereby the spring means can then act to urge the lancet forwards and momentarily project its tip.

2. A pricker as claimed in claim 1, wherein the guide means retain the lancet in a primed, spring-energised condition when said parts are in said initial position.

3. A pricker as claimed in claim 1, wherein the guide means are shaped to cause the lancet to shift relative to said one part, thereby to energise the spring means, as said parts are moved into said second position.

4. A pricker as claimed in claim 1, wherein the two parts are integrally moulded in plastics material, with a thin flexible bridge between them acting as a hinge.

5. A pricker as claimed in claim 1, wherein the lancet has a generally cylindrical body of moulded plastics material co-axially encasing a needle, the tip of the needle projecting from one end of the body and initially being protected by an integrally moulded cap breakable from the main body.

6. A pricker as claimed in claim 5, wherein said one part has means by which the lancet body can be held by one hand while the cap is removed by the other.

7. A pricker as claimed in claim 5, wherein the guide means co-operate with the lancet body and cap to remove the cap as said parts are moved towards said second position.

8. A pricker as claimed in claim 1, wherein means are provided to cause the lancet tip to retract immediately after its momentary projection.

9. A pricker as claimed in claim 8, wherein the retraction means are provided by a mouth of said other part through which the tip of the lancet momentarily projects, the mouth having a resilient tab which flexes to allow such projection but which immediately bends back to cause the retraction.

10. A pricker as claimed in claim 8, wherein the retraction means are provided by the spring means which are anchored to the lancet and to said one part.

11. A pricker as claimed in claim 1, wherein the two parts are locked together in said second position by the lancet bridging those parts within a virtually closed passage.

12. A pricker as claimed in claim 1, wherein the guide means are shaped to shield the tip so that it is virtually inaccessible when the forward end of the lancet is co-operating therewith.

* * * * *